United States Patent [19]
Ericcson et al.

[11] Patent Number: 5,869,023
[45] Date of Patent: Feb. 9, 1999

[54] COMPOSITION FOR MRI COMPRISING BOTH A POSITIVE AND A NEGATIVE CONTRAST AGENT

[75] Inventors: Anders Ericcson, Upsala, Sweden; Anne Kjersti Fahlvik, Oslo, Norway; Anders Hemmingsson, Upsala, Sweden; Mats Wikstrom, Ulm, Germany; Audun Øksendal, Oslo; Tore Bach-Gansmo, Jar, both of Norway

[73] Assignee: Nycomed Imaging AS, Oslo, Norway

[21] Appl. No.: 569,134

[22] PCT Filed: Jul. 11, 1994

[86] PCT No.: PCT/GB94/01500

§ 371 Date: Jan. 26, 1996

§ 102(e) Date: Jan. 26, 1996

[87] PCT Pub. No.: WO95/02831

PCT Pub. Date: Jan. 26, 1995

[30] Foreign Application Priority Data

Jul. 12, 1993 [GB] United Kingdom .................. 9314499

[51] Int. Cl.⁶ .................................... A61B 5/055
[52] U.S. Cl. ................. 424/9.36; 424/9.363; 424/9.364; 514/836
[58] Field of Search ................................ 424/9.36, 9.364, 424/9.363; 128/653.4, 654; 436/173; 514/836

[56] References Cited

U.S. PATENT DOCUMENTS

| | | | |
|---|---|---|---|
| 4,899,755 | 2/1990 | Lauffer et al. | 128/654 |
| 4,972,837 | 11/1990 | Engelstad et al. | 424/9 |
| 5,128,121 | 7/1992 | Berg et al. | 424/9 |
| 5,143,716 | 9/1992 | Unger | 424/9 |
| 5,190,744 | 3/1993 | Rocklage et al. | 424/9 |
| 5,318,771 | 6/1994 | Lauffer et al. | 424/9 |
| 5,368,839 | 11/1994 | Aime et al. | 424/9 |

FOREIGN PATENT DOCUMENTS

| | | |
|---|---|---|
| WO-A-86 06605 | 11/1986 | WIPO . |
| WO-A-89 09625 | 10/1989 | WIPO . |
| WO-A-91 14186 | 9/1991 | WIPO . |
| WO-A-91 16079 | 10/1991 | WIPO . |

OTHER PUBLICATIONS

Wiessleder et al., AJR 150:;561–566 (1988).

*Primary Examiner*—Gary E. Hollinden
*Attorney, Agent, or Firm*—Bacon & Thomas

[57] ABSTRACT

This invention relates to improvements in and relating to magnetic resonance imaging of the human or non-human body. The invention particularly relates to a method in which positive and negative contrast agents are administered to enhance image contrast.

15 Claims, 12 Drawing Sheets

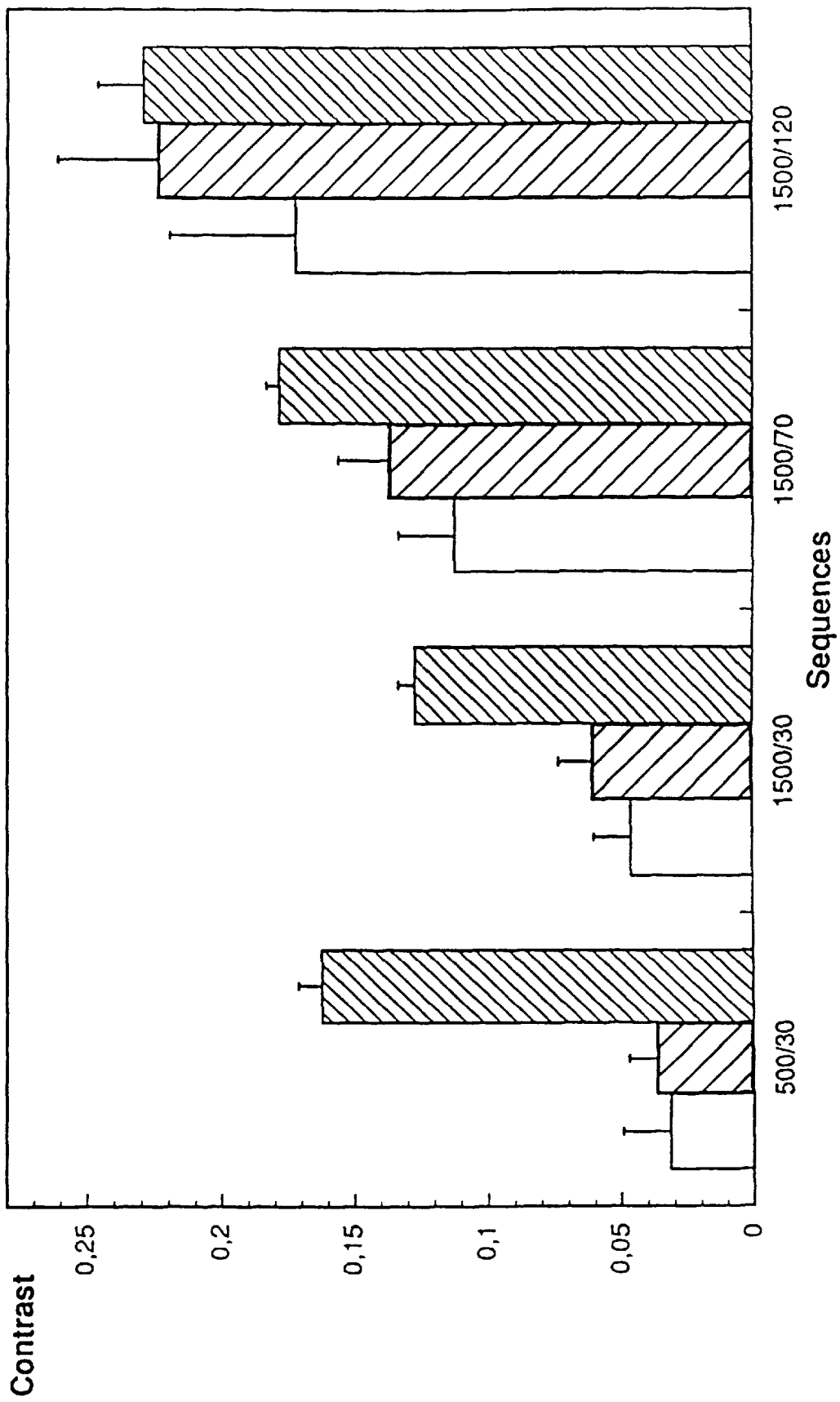

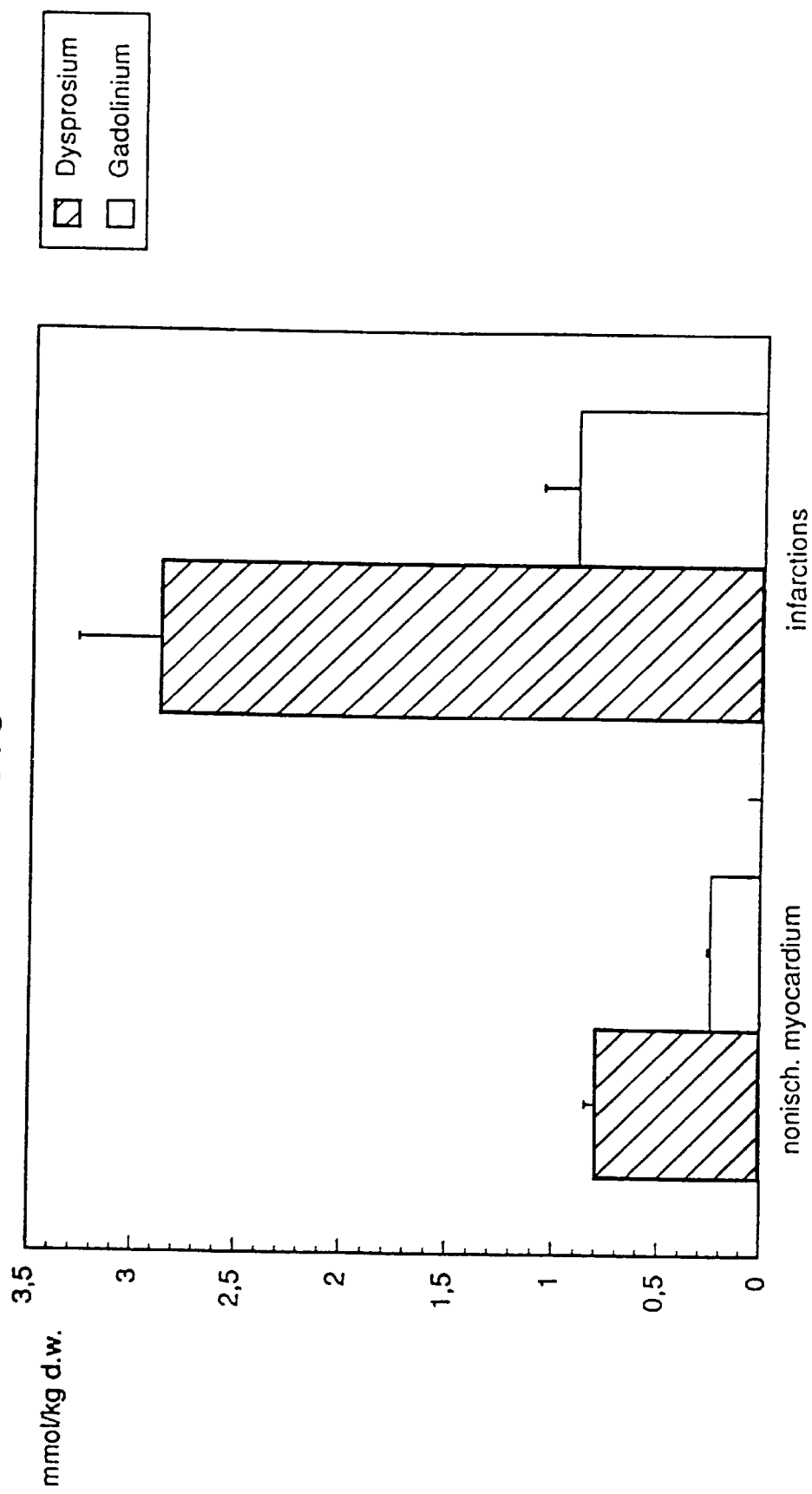

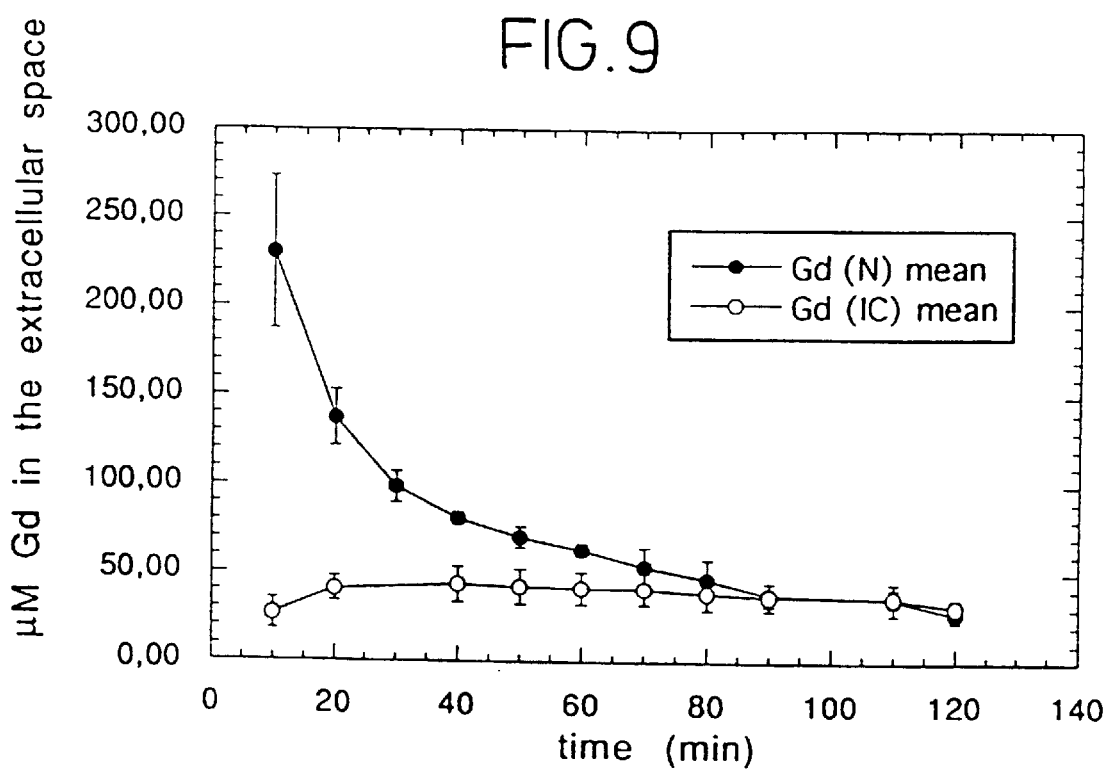
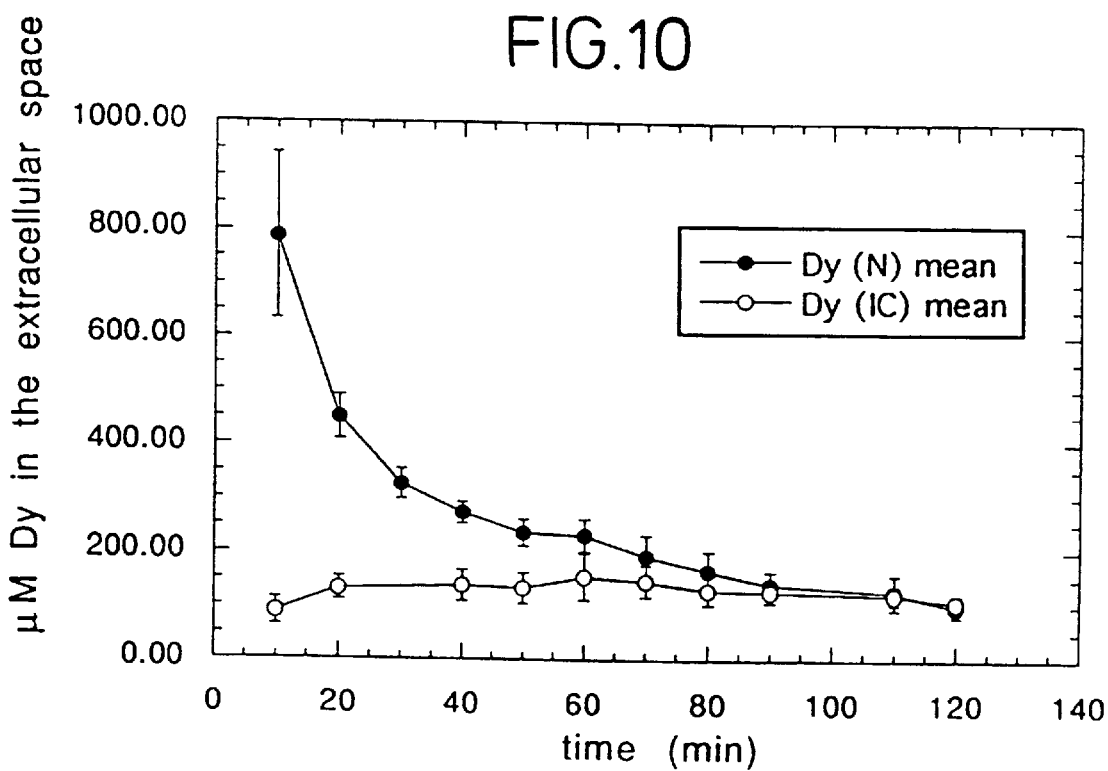

tissue content ratio (infarct/normal)

signal intensity ratio (infarct/normal)

COMPOSITION FOR MRI COMPRISING BOTH A POSITIVE AND A NEGATIVE CONTRAST AGENT

The present invention relates to improvements in and relating to magnetic resonance (MR) imaging of the human or non-human animal body, in particular to a method in which positive and negative contrast agents are administered to enhance image contrast.

In MR imaging, the contrast in the image generated may be enhanced by introducing into the zone being imaged an agent (a "contrast agent"), which affects the spin reequilibration characteristics of nuclei (the "imaging nuclei" which generally are protons and more especially water protons) which are responsible for the resonance signals from which the images are generated. The enhanced contrast thus obtained enables particular organs or tissues to be visualized more clearly by increasing or by decreasing the signal level of the particular organ or tissue relative to that of its surroundings. Contrast agents raising the signal level of the target site relative to that of its surroundings are termed "positive" contrast agents whilst those lowering the signal level relative to surroundings are termed "negative" contrast agents.

The majority of materials now being proposed as MR imaging contrast agents achieve a contrast effect because they contain paramagnetic or superparamagnetic species. The use of such materials as MR contrast agents has been widely advocated and broad ranges of suitable materials have been suggested in the literature.

Thus, for example Lauterbur and others have suggested the use of manganese salts and other paramagnetic inorganic salts and complexes (see Lauterbur et al. in "Frontiers of Biological Energetics", volume 1, pages 752–759, Academic Press (1978), Lauterbur in Phil. Trans. R. Soc. Lond. B289: 483–487 (1980) and Doyle et al. in J. Comput. Assist. Tomogr. 5(2): 295–296 (1981)), Runge et al. have suggested the use of particulate gadolinium oxalate (see for example U.S. Pat. No. 4,615,879 and Radiology 147(3): 789–791 (1983)), Schering AG have suggested the use of paramagnetic metal chelates, for example of aminopolycarboxylic acids such as nitrilotriacetic acid (NTA), N,N,N'N'-ehtylenediaminetetraacetic acid (EDTA), N-hydroxyethyl-N,N'N'-ethylenediaminetriacetic acid (HEDTA), N,N,N',N'',N''-diethylenetriaminepentaacetic acid (DTPA), and 1,4,7,10-tetraazacyclododecanetetraacetic acid (DOTA) (see for example EP-A-71564, EP-A-130934, DE-A-3401052 and U.S. Pat. No. 4,639,365), and Nycomed Imaging AS and Nycomed Salutar Inc. have suggested the use of paramagnetic metal chelates of iminodiacetic acids and other aminopolycarboxylic acids such as DTPA-BMA and DPDP (see EP-A-165728, WO-A-86/02841, EP-A-299795, EP-A-290047 and WO-A-90/08138). Besides paramagnetic metals, paramagnetic stable free radicals have also been suggested for use as positive MR imaging contrast agents (see for example EP-A-133674).

Other paramagnetic MR contrast agents are suggested or reviewed in, for example, EP-A-136812, EP-A-185899, EP-A-186947, EP-A-292689, EP-A-230893, EP-A-232751, EP-A-255471, WO-A-85/05554, WO-A-86/01112, WO-A-87/01594, WO-A-87/02893, U.S. Pat. Nos. 4,639,365, 4,687,659, 4,687,658, AJR 141: 1209–1215 (1983), Sem. Nucl. Med. 13: 364 (1983), Radiology 147: 781 (1983), J. Nucl. Med. 25: 506 (1984) and WO89/00557.

Superparamagnetic MR contrast agents (particulate negative contrast agents, e.g. sub-domain sized magnetic iron oxide particles either free or enclosed within or bound to a particle of a non-magnetic matrix material such as a polysaccharide) were disclosed by Schröder and Salford in WO-A-85/02772, by Nycomed AS in WO-A-85/04330, by Widder in U.S. Pat. No. 4,675,173, by Schering AG in DE-A-3443252 and by Advanced Magnetics Inc. in WO-A-88/00060.

While the utility of paramagnetic materials as positive MR contrast agents was recognized as early as 1978 by Lauterbur et al. (supra), the use of superparamagnetic and paramagnetic materials as negative MR contrast agents was not proposed until much later. Indeed the first paramagnetic MR contrast agents to be available commercially were positive agents such as the gadolinium chelates GdDTPA (Magnevist® from Schering), GdDTPA-BMA (Omniscan® from Nycomed Imaging AS), and GdHP-DO3A (ProHance® from Squibb). The positive nature of their contrast effect derives from the dominance of their $T_1$ reducing effect for the imaging nuclei at the concentrations at which they are used.

The first proposal of negative paramagnetic (as opposed to superparamagnetic) MR contrast agents was by Villringer et al. (see Mag. Res. in Med. 6:164–174 (1988)) who showed that the magnetic susceptibility varying effect of high magnetic moment paramagnetic species, such as Dy(III), could be used to generate contrast. Such paramagnetic magnetic susceptibility or $T_2^*$ agents have since been widely proposed for use as negative MR contrast agents for the study of many aspects of anatomy and body function (see for example WO-A-91/14186 (Kucharczyk) which discusses the use of such agents in the study of blood flow abnormalities associated with ischaemia).

The use of both positive and negative contrast agents to achieve a so-called double contrast effect was in due course proposed. It was shown that the positive agent could be used to enhance the MR signal from the body zone into which it distributes while the negative agent would suppress the MR signal from the zone it distributes into, thus enhancing contrast between the zones where they are not physically or temporally coextensive.

Intravenous administration, at separate times, of the positive contrast agent Gd DTPA-dimeglumine (which following such administration rapidly distributes throughout the extracellular fluid (ECF)) and of superparamagnetic ferrite particles (which being particulate are rapidly extracted from the blood by the reticuloendothelial system) was proposed by Weissleder et al. (see AJR 150: 561–566 (1988)) for imaging of liver cancers and by Carvlin et al. (see Society for Magnetic Resonance Imaging, 5th Annual Meeting, San Antonio, 1987) for studying renal bloodflow.

With one agent distributing into the extracellular fluid, i.e. being an ECF agent, and the other being constrained to the circulatory and RES systems (i.e. being a body duct- or tissue-specific agent), this double contrast technique relied upon the differences in the spatial distributions of the two contrast agents to generate the contrast enhancement.

Berg et al. (see WO-A-89/09625) subsequently proposed a double contrast technique in which body duct-specific positive and negative contrast agents were used but with contrast enhancement arising from spatial or temporal differences in distribution due to the separate administration of the agents or to the different biodistribution characteristics of the agents used. Thus, by way of example, coadministration of superparamagnetic particles which accumulate in the liver and of Cr-HIDA, a positive agent which concentrates in the bile, facilitated visualization of the bile ducts (see Berg (supra) and Hemmingsson et al. SMRM 7: 796 (1988)).

A further development of the double contrast technique was to use sequentially administered positive and negative ECF agents with the second agent being administered only after the first had been allowed sufficient time to accumulate in the infarcted tissue. Thus if an ECF agent is allowed to circulate for a prolonged period within a body having diseased or damaged tissue the agent may accumulate within that tissue. If image generation is then affected shortly after the administration of the second agent (e.g. less than 5 minutes after) then the first agent will enhance the image of the diseased or damaged tissue while relatively speaking the second agent enhances only the normal tissue. Wikstrøm (see "MR imaging of experimental myocardial infarction", PhD thesis, Uppsala University, Sweden 1992, published at Acta Radiol Suppl. 33 S379:1–30 (1992)) described the use of such a double contrast technique in the study of myocardial infarction. The first, positive agent GdDTPA-BMA distributed to the infarcted area of the heart while the second, negative agent Dy DTPA-BMA was allowed essentially only to distribute to the normal tissue resulting in the generation of enhanced contrast between normal and infarcted tissue.

The present invention arises from the recognition that coadministration of positive and negative agents which distribute to the same body spaces, despite the identical biodistributions and directly opposed contrast effects, can, by virtue of the different mechanisms of contrast enhancement, provide a further double contrast image enhancement technique for use in determining tissue viability or injury.

ECF agents, by definition, distribute into the extracellular fluid space (the vascular bed and the interstitium) and do not enter the intracellular compartment. Water diffusion across cell membranes however does occur and it is found that the positive ECF agents exert their $T_1$ relaxation effect not only on water protons in the extracellular fluid but also on those in the intracellular fluid. However, the $T_2^*$ effect on which negative contrast is founded generally requires a local concentration gradient for the $T_2^*$ agent and thus in biological structures the signal strength reduction only occurs for a compartmentalized system, such as the cellular system of body tissue. The surprising finding on which the present invention is based is that the signal enhancement of the positive agent can be made compartmentalization dependent, even in $T_1$ weighted images, by coadministration of a negative $T_2^*$ agent thus achieving enhanced contrast between normal tissue and tissue in which cell membrane integrity has been reduced or destroyed, e.g. between healthy, viable and non-viable tissue.

Cells with some reduction in membrane integrity may still remain viable if corrective action is taken in due time, e.g. reperfusion of ischemic tissue, but serious reduction in integrity is associated with cell death. Reduction of loss of cell membrane integrity is readily detected, e.g. by assays for released enzymes, but imaging of areas of membrane integrity loss, and in particular of an area at risk between viable and non-viable tissue, has not hitherto been straightforward.

Thus viewed from one aspect the present invention provides a method of generating an enhanced image of a human or non-human, preferably mammalian, animal body which comprises parenterally administering to said body a contrast medium composition comprising at least two extracellularly distributing paramagnetic contrast agents which distribute to substantially the same body volume, one of said agents being a positive contrast agent and another being a negative contrast agent, and generating a magnetic resonance image of at least a part of said body into which said contrast agents distribute.

Viewed from a further aspect the invention also provides a diagnostic image contrast enhancing composition for parenteral administration for use in magnetic resonance imaging of a human or non-human animal species comprising at least two physiologically tolerable, extracellularly distributing, paramagnetic contrast agents which distribute to substantially the same body volume in said species, one of said agents being a positive agent and a second being a negative agent.

The positive ($T_1$) and negative ($T_2^*$) agents used according to the invention should distribute extracellularly to the same body volume. Preferably they are true ECF agents which distribute into the extracellular fluid space, i.e. both within the blood plasma and within the interstitium (the space both out side the vascular bed and outside the cells). However where tissue damage is such that the barrier between the capillary bed and the interstitium is breached, macromolecular and particulate agents (e.g. blood pool agents) which normally are kept within the vascular bed (at least up to their extraction or excretion therefrom by the liver or kidney) will function according to the invention as these will then penetrate to the interstitium in the region of interest. The negative agent used according to the invention should be a $T_2^*$, compartmentalization-dependant, agent and both positive and negative agents will generally take the form of compounds or complexes of transition metal or lanthanide metal ions.

Although the positive and negative contrast agents are preferably coadministered, the double contrast technique of the invention may nonetheless be effected with separate administration as long as the relative timing of contrast agent administration and image acquisition is not such that the distribution pattern of the first administered agent in the body zone of interest is significantly different from that of the second agent, i.e. as in the Wikstrøm technique discussed above.

Thus viewed from a further aspect the invention provides a method of generating an enhanced image of a human or non-human, preferably mammalian, animal body which comprises parenterally administering to said body a first and a second extracellularly distributing paramagnetic MR contrast agent having substantially the same biodistribution, preferably ECF agents but also for example blood pool agents, and generating a magnetic resonance image of a part of said body into which both of said agents have distributed with a substantially uniform concentration ratio therebetween, preferably a part of the body in which both of said agents enter the interstitium, one of said agents being a positive agent and the other being a negative agent. In this method, the first and second agents may be administered separately or, preferably, together.

The two agents should preferably be so administered that, at the time image acquisition is effected, the concentration of the negative agent at a damage site of interest is such that a positive contrast effect is achieved by the combination of the agents, with signal enhancement (at least in $T_1$ weighted sequences) for damaged tissue and a lesser enhancement, no enhancement, or a signal reduction (in the same sequences) for normal tissue.

In the example of the ischaemic heart, where positive and negative ECF agents are administered sequentially (e.g. to allow generation of an image enhanced by only one agent, generally the positive agent, before generation of the double contrast image), the first agent will generally be administered about 5 to 20 minutes before generation of a single-contrast enhanced image with the second agent being administered shortly thereafter (e.g. 0–10 minutes) and the double-contrast image being generated from the MR signals detected 5 to 20 minutes after its administration. The two agents will preferably be introduced at the same site. For other systems where contrast agent accumulation is short lived, e.g. liver metastases, if the two agents are administered sequentially, the gap will be kept as short as possible, e.g. less than about 3 minutes.

A particular benefit of the double contrast technique of the invention is to harness for $T_1$ weighted imaging the compartment-dependent contrast possible with $T_2^*$ susceptibility imaging using a negative agent. While a negative agent, such as DyDTPA-BMA, may inherently have the potential to enhance contrast between viable and non-viable tissue compartments, in $T_2^*$ susceptibility imaging the choice of available pulse sequences is limited (generally to $T_2^*$- or $T_2$-weighted sequences) and the image quality is often poor due to low signal to noise ratio. In very many situations, especially when small lesions are being investigated, anatomical detail and intertissue contrast is much superior in $T_1$-weighted images and thus the use of positive, signal strength enhancing contrast agents in sequences allowing superior signal intensity and resolution is preferred.

As demonstrated below however, in positive contrast agent enhanced $T_1$-weighted imaging, by concurrent use of the negative $T_2^*$ agent, contrast enhancement in tissue in which cell membrane integrity varies, e.g. between viable and non-viable tissue, can be obtained. The imaging techniques used in the methods of the invention may be any of the known techniques, but particularly preferably are spin echo, fast spin echo, gradient echo, fast gradient echo, echo planar imaging and other techniques, being $T_1$-weighted, $T_2$-weighted, $T_2^*$-weighted, or intermediate-weighted (e.g. "proton density") sequences and most preferably $T_1$-weighted sequences.

In an uncompartmentalized system (i.e. a one compartment system), e.g. cell-free water, containing negative and positive agents in the molar concentrations discussed below in Example 2, the $T_2^*$ effect of the negative contrast agent would be negligible compared with the $T_1$, signal enhancing, effect of the positive agent. However, for a sample containing living cells disposed in an aqueous fluid and accounting for the majority (e.g. 80%) of the sample volume, and having positive and negative agents at the same overall concentrations but restricted in distribution to the extracellular fluid, the $T_2^*$ effect of the negative agent will dominate. This provides a reasonable model for normal tissue. If however the cell walls in the sample are damaged, the relative importance of the $T_1$ signal enhancing effect as opposed to the $T_2^*$ signal suppressing effect is increased and thus the combination of positive and negative agents is able to provide particularly effective enhanced contrast between viable and non-viable tissues since the contrast can be between black (viable tissue—$T_2^*$ dominant) and white (tissue without cell membrane integrity—$T_1$ dominant) as compared with black to grey for the negative agent alone or white to white for the positive agent alone.

A practical example of this use of the combination of positive and negative agents is in examination for metastases shortly after radiation therapy or chemotherapy, i.e. to provide an indication of successful treatment, especially in the liver. The positive agent on its own would provide signal enhancement for the liver as a whole and would not provide contrast between living and non-viable tissues. Using a negative agent alone the normal liver tissue and viable metastatic tissue will provide a heavily suppressed signal (black) while non-viable metastatic tissue may show up as greyish due to the lack of compartmentalization and the resultant ineffectiveness of the $T_2^*$ effect. Nonetheless the $T_2^*$-weighted sequences required to show this relatively poor contrast will only provide poor resolution and poor contrast to noise levels. Accordingly the effectiveness of the negative agent on its own in the search for small lesions is extremely limited. Using positive and negative agents together however allows higher resolution, $T_1$-weighted sequences to be used and non-viable metastatic tissue will show up clearly as a region of increased signal strength, e.g. as a white spot in a region of low background signal. Regions of reversible tissue damage at the periphery of irreversible tissue damage may likewise show up as grey zones between white (healthy) and black (dead or non-viable) zones. Also, a region with no or very subtle changes after Dy administration may both be the result either of non-compartmentalisation (non-viable) or a lack of distribution of the contrast agent (as is sometimes observed in non-viable tissue).

The double contrast technique will show an effect of Gd in such a region if contrast distribution does occur. Thus three possible diagnostic outcomes may follow double contrast distribution: viable, non-viable or non-perfused tissues.

The double contrast imaging methods of the invention are applicable generally to studies of damaged or non-viable tissue but are especially applicable to studies of tumors, abscesses, or ischemic cells in areas such as the CNS, heart, liver and musculoskeletal system. Since cell membrane permeability to ECF agents is enhanced even before cell death, the methods of the invention make it possible to assess the severity as well as the spatial extent of the condition.

The method of the invention is also well suited for use in monitoring and guiding radiation and chemotherapeutic treatment of tumours, e.g. liver or CNS metastases. Where multiple lesions occur in an organ, the treatment of choice tends to be radiotherapy or chemotherapy rather than surgery. The double contrast imaging technique of the invention provides an early post-treatment means of identifying the cytotoxic efficacy of the treatment and thus allows the chemotherapeutic or radiation treatment to be continued or varied so as to optimize its long term success.

The paramagnetic blood pool and ECF contrast agents used according to the invention are preferably physiologically tolerable and may be any of the many paramagnetic compounds known as blood pool agents or known to distribute into the interstitium.

Generally however such compounds will be complexes, preferably water-soluble complexes, of paramagnetic transition metal or lanthanide metal ions, e.g. ions of metals having atomic numbers of 21 to 29, 42, 44 and 57 to 71. Chelate complexes of such metal ions, e.g. with aminopolycarboxylic acid chelants such as those described in the patent literature by Nycomed Imaging, Nycomed Salutar, Guerbet, Mallinckrodt, Schering and Squibb, are especially preferred, in particular complexes with tri, tetra or penta-aza macrocyclic ligands such as DOTA and its derivatives DO3A, HPDO3A etc., and complexes with linear chelants such as DTPA and DTPA-BMA.

As positive agents, complexes of Gd, Fe, Ho, Mn, Cr and Er, especially $Gd^{3+}$, $Cr^{3+}$, $Fe^{3+}$ and $Mn^{2+}$ are especially preferred and as negative agents complexes of Tb, Sm or Dy, especially $Dy^{3+}$, are particularly preferred.

In order to establish a substantially equal distribution pattern for the positive and negative agents, it is especially preferred that the complexing agent is the same for both, e.g. by use of the combination of GdDTPA-BMA and DyDTPA-BMA etc.

As mentioned above the positive and negative agents are preferably ECF agents, i.e. agents which distribute generally within the extracellular space including both the vascular bed and the interstitium. However, agents which are normally restricted to the blood pool may be used for imaging tissue damage which involves disruption of the blood pool:interstitium barrier as in such cases the blood pool agents will distribute into the interstitium at the site of interest.

While the positive and negative agents are conveniently different species (e.g. DyDTPA and GdDTPA), in one embodiment of the invention it is envisioned that a single species may provide both agents. This can be done for example with polychelants (such as those described by Nycomed Salutar in WO-A-90/12050, WO-A-91/05762 and WO-A-93/06868) loaded with two or more different paramagnetic metal ions, e.g. Dy and Gd in an appropriate mole ratio (e.g. a ratio as described below for the discrete positive and negative agents).

While many chelating agents appropriate for the preparation of chelates are known and described in the literature, e.g. in the patent specifications mentioned above, it may be of assistance to note that many of the preferred chelants will generally be of formula I

$$A\,[X\,(CR_2)_n]_m\,XA \qquad (I)$$

where each A independently is a hydrogen atom or a hydrophilic, lipophilic or metal ion-complexing group (e.g. a $C_{1-6}$alkyl group optionally substituted by $C_{1-6}$alkoxy, hydroxy, amine, carboxyl or amide groups) or two A groups on different X's together form a $(CR_2)_n$ bridging group, and preferably two or three A groups are metal-ion complexing groups, especially carboxyalkyl groups; each X independently is oxygen, sulphur or $N[(CR_2)_nX]_pA$, preferably NA;

m is 0 to 6, preferably 1, 2 or 3;

each n independently is 1, 2 or 3, preferably 2;

p is 0 to 3, preferably 0 or 1;

and each R independently is a hydrogen atom or a lipophilic or hydrophilic group (e.g. as described for A) or two R's together represent a $C_{1-4}$ alkylene bridge optionally interrupted by an oxygen or sulphur atom or a group NA.

In the performance of the methods of the invention, the dosages of positive and negative agents used will of course depend on the precise nature of the contrast agents used as well as on the size and species of the subject under investigation and the nature of the cells whose viability is being investigated. Typically the positive and negative agents will be used at a mole ratio of from 1:1 to 1:10 (relative to the paramagnetic centres, e.g. metal ions), e.g. 1:2 to 1:6, especially 1:3 to 1:4 and the double contrast compositions according to the invention which are intended for use in simultaneous administration of positive and negative contrast agents will advantageously contain both agents in these relative proportions. Generally the contrast media compositions as administered will contain from 0.001 to 5.0, preferably 0.1 to 2, especially 0.2 to 1.0 and most especially 0.3 to 0.7 moles/liter of paramagnetic species (e.g. complexed metal ion), whether formulated for separate or unitary administration.

Typically the dosage for the positive agent will be in the range 0.01 to 0.7 mmol, 0.05–0.3, (paramagnetic metal)/kg bodyweight while that for the negative agent will be in the range 0.075 to 3.0, preferably 0.2 to 2.0 mmol/kg.

The contrast agents, whether formulated for simultaneous or separate administration, may be formulated with conventional pharmaceutical or veterinary formulation aids, for example stabilizers, antioxidants, osmolality adjusting agents, buffers, pH adjusting agents, etc., and may be in a form suitable for parenteral administration, for example injection or infusion, or a form suitable for dilution or dissolution to produce a parenterally administrable composition. Thus the contrast agent compositions may be in conventional pharmaceutical administration or pre-administration forms such as powders, solutions, suspensions, dispersions, etc.; however, solutions in physiologically acceptable carrier media, for example water for injections, will generally be preferred.

The contrast media according to the invention may therefore be formulated for administration using physiologically acceptable carriers or excipients in a manner fully within the skill of the art. For example, the chelate components, optionally with the addition of pharmaceutically acceptable excipients, may be suspended or dissolved in an aqueous medium, with the resulting solution or suspension then being sterilized. As mentioned above, suitable additives include, for example, physiologically biocompatible buffers (as for example, tromethamine hydrochloride), slight additions of other chelating agents (as for example, diethylenetriaminepentaacetic acid) or, optionally, calcium or sodium salts (for example, calcium chloride, calcium ascorbate, calcium gluconate or calcium lactate) or complexes (e.g. calcium complexes of one of the complexing agents used to complex the paramagnetic metal species). (The use of added calcium complexes to reduce contrast agent composition toxicity is discussed in WO-A-90/03804 (Nycomed Salutar) ).

Parenterally administrable forms, e.g. intravenous solutions, should be sterile and free from physiologically unacceptable agents, and should have low osmolality to minimize irritation or other adverse effects upon administration and thus the contrast media should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in REMINGTON'S PHARMACEUTICAL SCIENCES, 15th ed., Easton: Mack Publishing Co., pp 1405–1412 and 1461–1487 (1975) and THE NATIONAL FORMULARY XIV, 14th ed. Washington: American Pharmaceutical Association (1975). The solutions can contain preservatives, antimicrobial agents, buffers and antioxidants conventionally used in parenteral solutions, excipients and other additives which are compatible with the chelates and which will not interfere with the manufacture, storage or use of products.

As mentioned above the contrast agent compositions may also, of course, be in concentrated or dried form for dilution prior to administration.

BRIEF DESCRIPTION OF THE DRAWINGS

FIG. 7 shows the contrast ratios between infarcted and non-ischemic myocardium in excised hearts. The sequences TR/TE 500/30, 1500/30, 1500/70 and 1500/120 are compared in the control (n=6, white bars, Dy-DTPA-BMA (2 hour post-injection 0.1 mmol/kg b.w., n=6, black bars) and double-contrast groups (n=5, hatched bars). Each bar represents a mean value, with error bars=1 SD.

FIG. 8 is a bar graph which shows the measured distribution of gadolinium and dysprosium in infarcted and non-infarcted myocardium.

FIGS. 9 and 10 are graphs which show the kinetics of gadolinium and dysprosium distribution within the extracellular space in terms of the concentrations of gadolinium and dysprosium in microdialysate from infarcted (IC) and non-ischemic myocardium (N) monitored in vivo.

The compositions and methods of the invention will now be described further with reference to the following non-limiting Examples.

EXAMPLE 1

Combined ECF Contrast Agent Solution 100 ml of solution containing:

| | |
|---|---|
| Gd DTPA-BMA | 0.5 mmol/ml |
| Dy DTPA-BMA | 1.5 mmol/ml |
| NaCa DTPA-BMA | 0.1 mmol/ml |
| Water for injections | ad 100 ml |

A dosage of 60 ml of this solution would generally be administered to an adult human. DTPA-BMA and its Gd and CaNa complexes were prepared as described in WO-A-90/03804 (Nycomed Salutar) and the Dy complex was prepared analogously.

EXAMPLE 2

In vitro Comparative Tests

Human blood samples with different hematocrit readings (Ht) of 27%, 45% and 69% were prepared to provide sample models for different levels of compartmentalization between intracellular and extracellular fluids. To initiate cellular level injury, samples with these Ht readings were frozen to effect cell membrane destruction. Finally a control sample of cell free plasma was also used.

To the test samples were added (a) a positive ECF contrast agent (GdDTPA-BMA at a dosage corresponding to 0.2 mmol Gd/kg); (b) a negative ECF contrast agent (DyDTPA-BMA at a dosage corresponding to 0.6 mmol Dy/kg); and (c) a positive ECF contrast agent and a negative ECF contrast agent (GdDTPA-BMA and DyDTPA-BMA at dosages corresponding to 0.2 mmol Gd/kg and 0.6 mmol Dy/kg).

Figure 1:
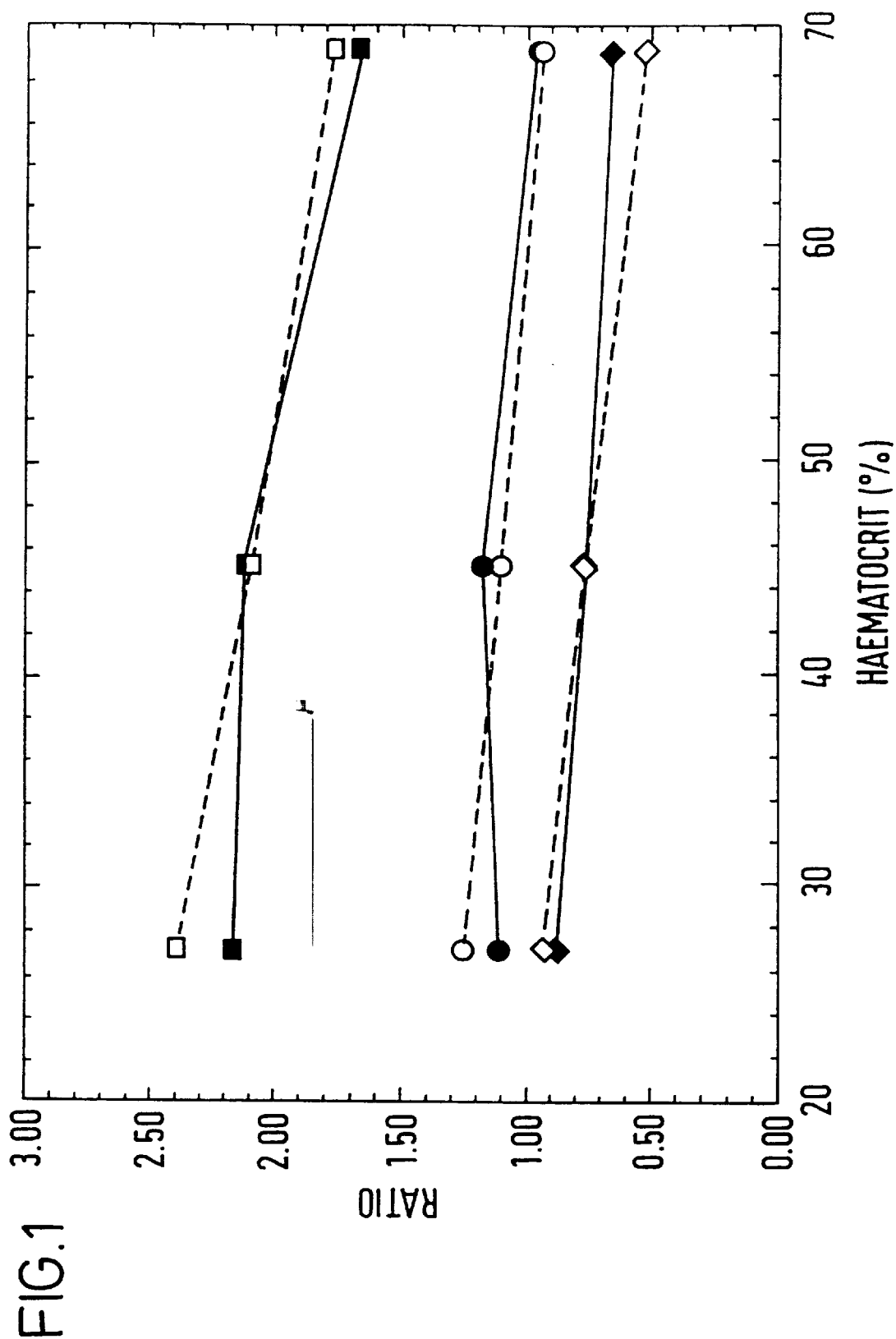
FIGS. 1–3 are graphs which show the ratios for different contrast agent doped samples on the vertical axis versus the percent hematocrit on the horizontal axis. The signal intensity for each contrast agent doped sample was normalized to the corresponding undoped sample and the results are set forth as the ratios shown in FIGS. 1–3.
Figure 2:
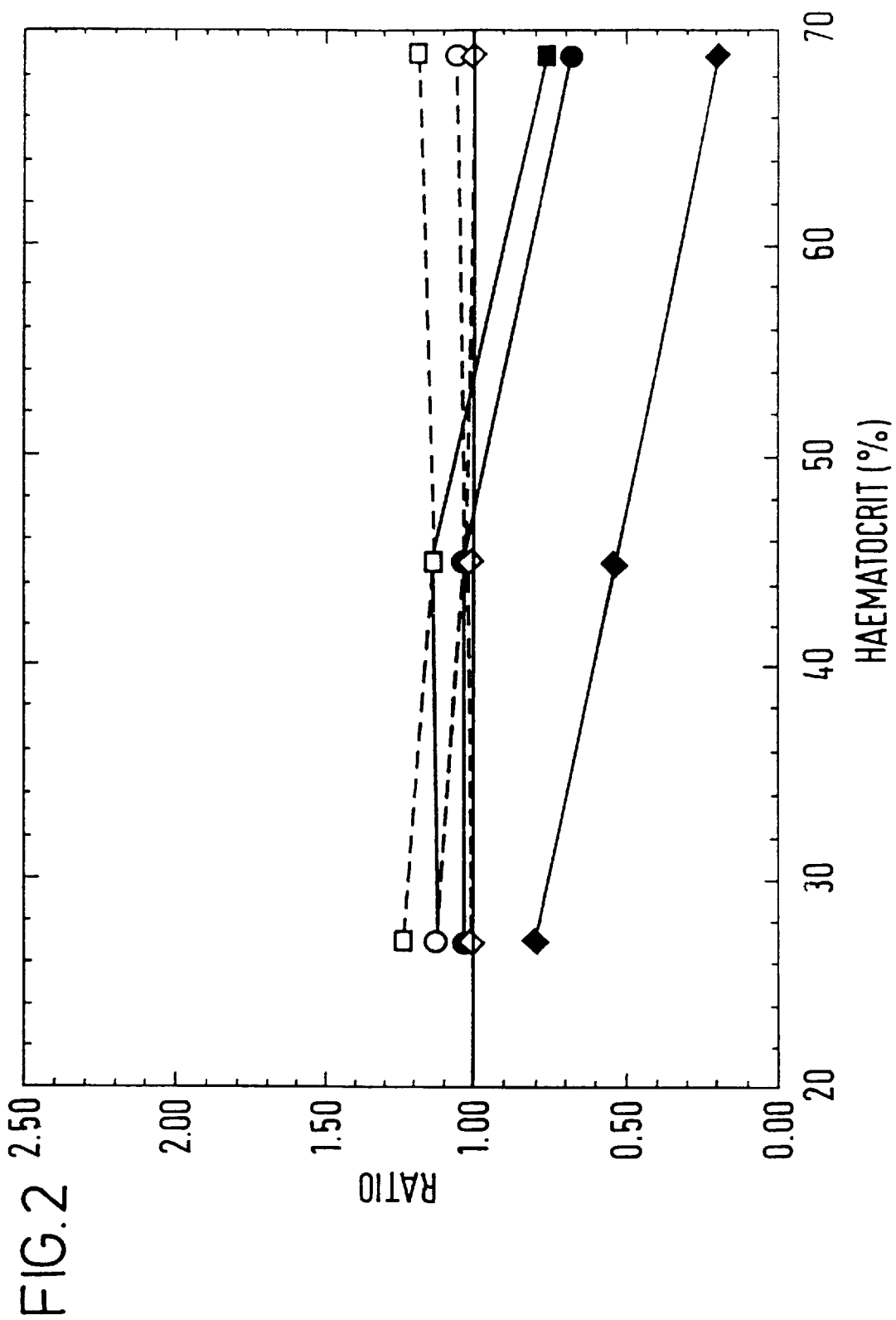
Figure 3:
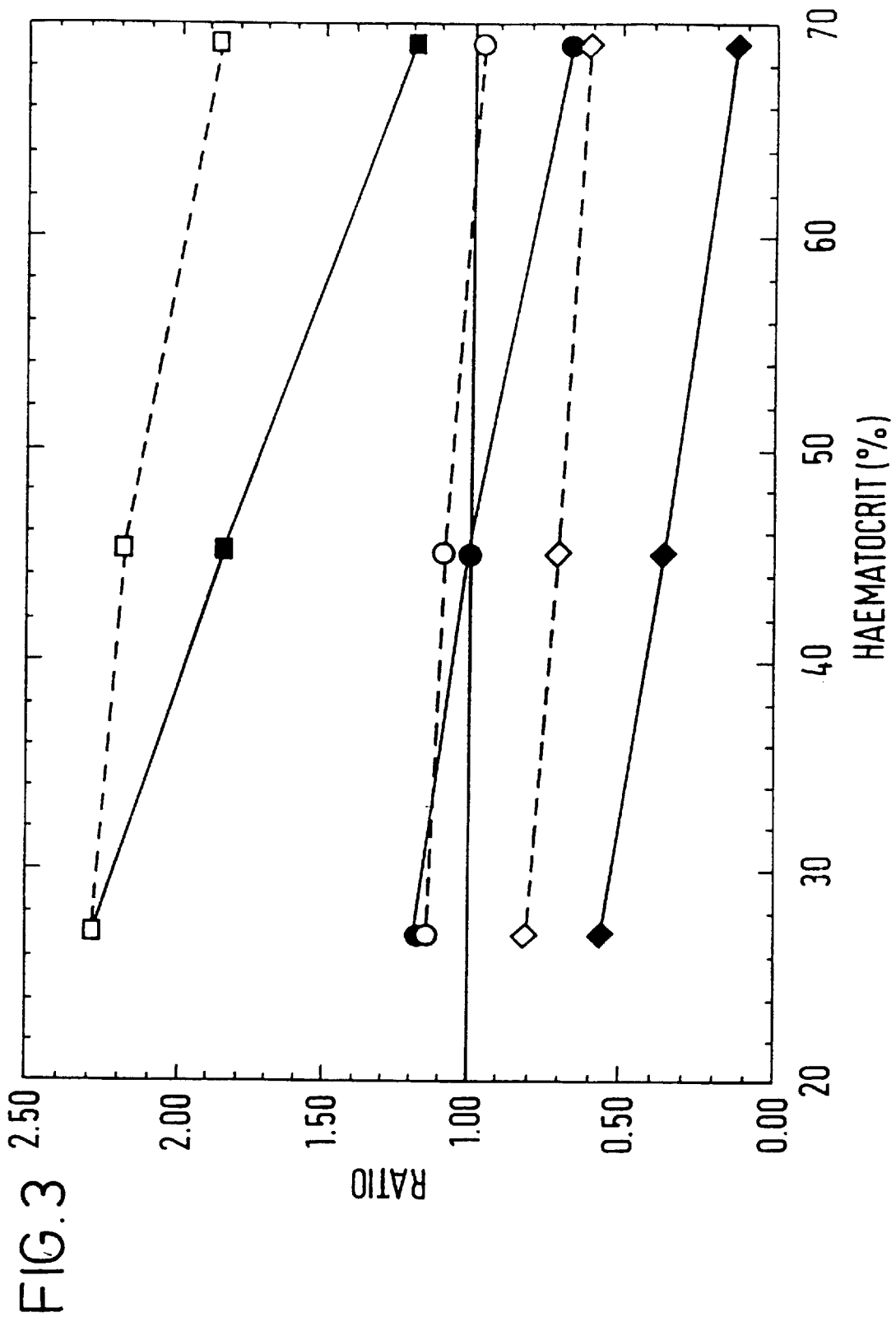

These doped samples, and controls to which no contrast agent was added, were imaged together at ambient temperature in the head coil of a Siemens Magnetom operating at 0.5 T using $T_1$-weighted (TR/TE 500/30 ms), $T_2$-weighted (TR/TE 1500/90 ms) and proton density-weighted (TR/TE 1500/30 ms) echo sequences. The signal intensity for each contrast agent doped sample was normalized to the corresponding undoped sample and the results are set forth as ratios in FIGS. 1 to 3 hereto, squares, circles and diamonds representing the ratios for $T_1$-weighted, PD-weighted and $T_2$-weighted sequences respectively.

For the positive agent used alone (see FIG. 1), an increased signal intensity effect was noticed in the $T_1$ weighted sequence but this effect was barely noticed in the other sequences and there was no significant discrimination between "viable" (solid symbols) and "non-viable" (hollow symbols) samples.

For the negative agent used above (see FIG. 2), the contrast agent had no effect on the "non-viable" samples whereas the signal intensity fell with increasing Ht reading for the "viable" sample in all sequences, but most markedly in the $T_2$-weighted sequence.

The combination of positive and negative agents gave similar results to the positive agent alone for the "non-viable" sample, again showing particular signal intensity increase in the $T_1$-weighted sequence. However, for the $T_2$- and PD-weighted sequences, the results for the "viable" sample were similar to those obtained with the negative agent alone. Moreover at the higher Ht readings, in particular for the $T_1$-weighted sequences, the signal intensities for the "non viable" sample were closely similar to those for the positive agent above.

These higher Ht readings provide a model for normal tissue, and indicate that using the method of the invention it may be possible to achieve strong "white-to-black" contrast between non-viable and viable tissue. This contrast is available in the higher spatial resolution, and thus more preferred, $T_1$-weighted imaging sequences where it is not achievable by use of positive or negative agents alone.

EXAMPLE 3

Combined Blood Pool Contrast Agent Solution

| | |
|---|---|
| Polylysine-polyDOTA-polyGd | 1 mmol Gd/ml |
| Polylysine-polyDOTA-polyDy | 3 mmol Dy/ml |
| Water for injections | ad 100 ml |

The polylysinepolyDOTA chelants are prepared and metallated as described by Nycomed Salutar in WO-A-90/12050.

EXAMPLE 4

Comparative Tests—Pig Heart Infarction Model

Myocardial infarction develops secondary to thrombotic occlusion of a previously diseased but patent coronary artery in most patients. Intervention aimed at salvaging ischemic myocardium, such as thrombolysis to re-establish blood flow or angioplasty, must be timed early to be beneficial. In the evaluation of such interventions, there is a need of an imaging method that at an early stage can identify and quantitate the occluded versus the reperfused (viable) vascular bed at the area at risk. A porcine model of 6-hour-old myocardial infarction demonstrated an infarct accumulation of extracellularly distributed contrast media, such as Gd-DTPA and Gd-DTPA-BMA, while the infarct periphery and nonischemic myocardium was preferentially enhanced after administration of the macromolecular contrast agent Gd-DTPA-labeled dextran. The negative, nonionic, contrast agent Dy-DTPA-BMA improves the infarct detection due to susceptibility-induced loss of signal intensity in nonischemic myocardium. Gd-DTPA-BMA-induced enhancement of the infarct signal combined with Dy-DTPA-BMA-induced loss of signal intensity in nonischemic myocardium results in excellent infarct conspicuity both in T1- and T2-weighted sequences. On the other hand, accumulation of Dy-DTPA-BMA in infarcted myocardium does not seem to result in signal loss but maintains a persistent intensity relative to the depleted signal in normal myocardium, due to the loss of cell membrane integrity.

Myocardial infarctions were induced in four pigs (25–30 kg) by placing a ligature around a diagonal branch of the left anterior descending (LAD) artery. The appearance of cyanosis distal to the ligature was used as a criterion of successful occlusion. Four hours post occlusion the selected contrast agent or contrast agent combination was given i.v. and the pigs were sacrificed two hours later. A control group received no contrast agent.

Following sacrifice, the hearts were extirpated and rinsed in isotonic saline to remove remaining blood. The hearts were examined ex vivo at ambient temperature in the MR equipment and then cut into thin transverse slices and soaked for about 20 minutes in a 1% aqueous solution of triphenyltetrazolium chloride (TTC) at 37° C. The slices were then visually inspected for unstained areas corresponding to infarction.

MR examination was performed in a superconductive whole body equipment (Siemens Magnetom) operating at 0.5 T. The hearts were investigated with saggital and transverse multi-slice spin-echo images with TR/TE of 500/30 (two excitations), 1500/30,70 and 1500/30,120 (single excitations) using a saddle-shaped coil with a diameter of 13 cm. The following parameters were used: Slice thickness 7 mm. Interslice gap 20%. Acquisition matrix 256×256 giving a resolution of 0.7×0.7 mm.

The total amount of Gd and Dy in infarcted and nonischemic myocardium was quantified by ICP-AES (inductively coupled plasma-atomic emission spectrometry).

In the transverse images regions of interest (ROI's) were placed in infarcted and nonischemic myocardium, in a corn oil phantom and in front of the heart (noise). The mean signal intensity (SI) was measured in each ROI.

In addition, the SD was measured in the noise. The measurements were used to calculate the contrast and the contrast-to-noise (C/N) ratios between infarcted (inf) and nonischemic (nonisch) myocardium and signal-to-noise (S/N) ratios using the following formulae:

$$\text{Contrast} = \frac{SIinf - SInonisch}{SIinf + SInonisch}$$

$$C/N = \frac{SIinf - SInonisch}{SD_{noise}}$$

$$S/N = \frac{SIcorn\ oil}{SD_{noise}}$$

The relaxation times in blood at 37° C. were calculated using a 0.47 Tesla Brucker Minispec before and repeatedly after administration of the contrast agent.

Figure 4:
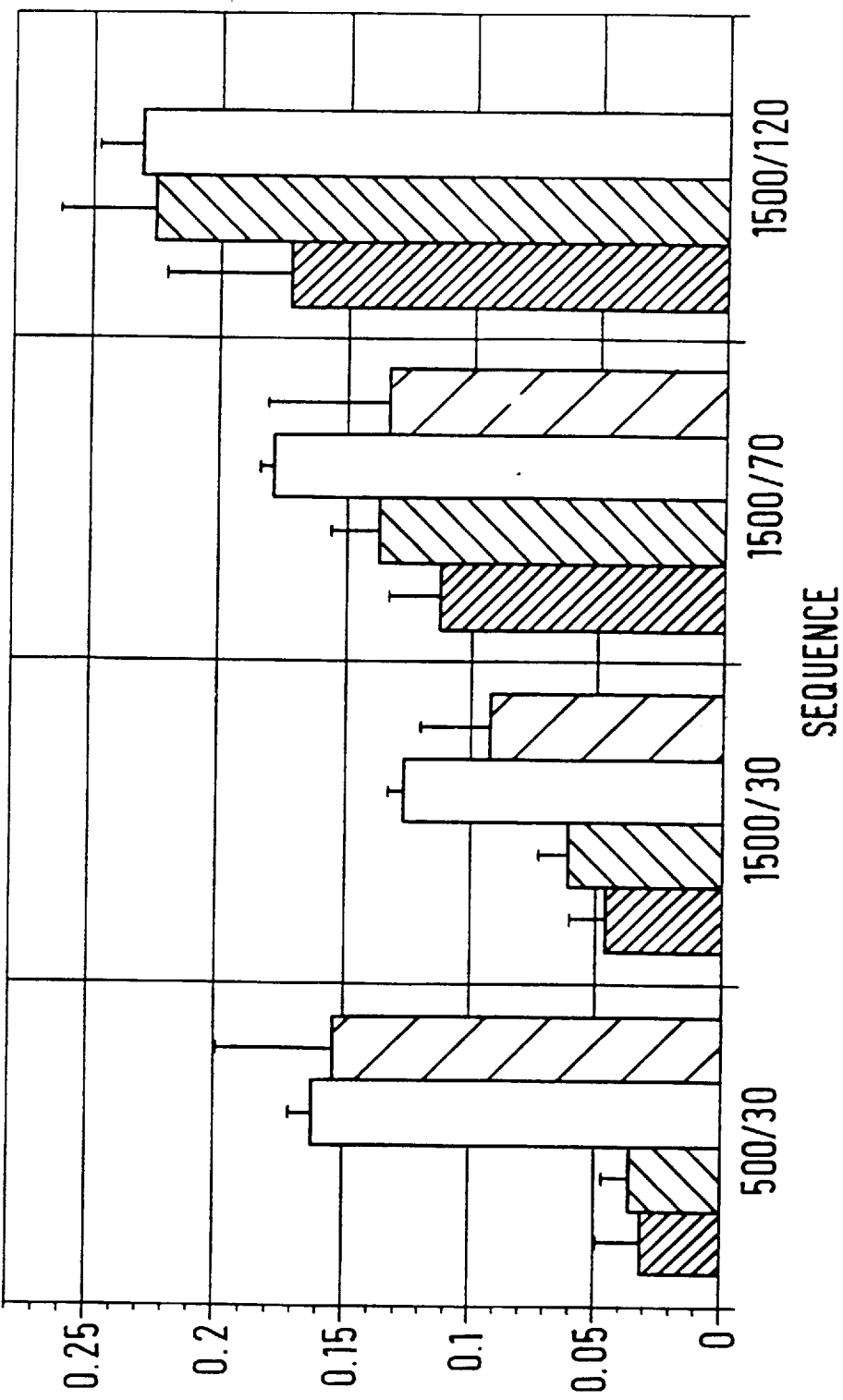
FIGS. 4 and 5 are bar graphs which show the contrast and C/N values as determined in example 4 for four study groups at the different TR/TE sequences running from $T_1$-weighted at 500/30 to $T_2$-weighted at 1500/120.
Figure 5:
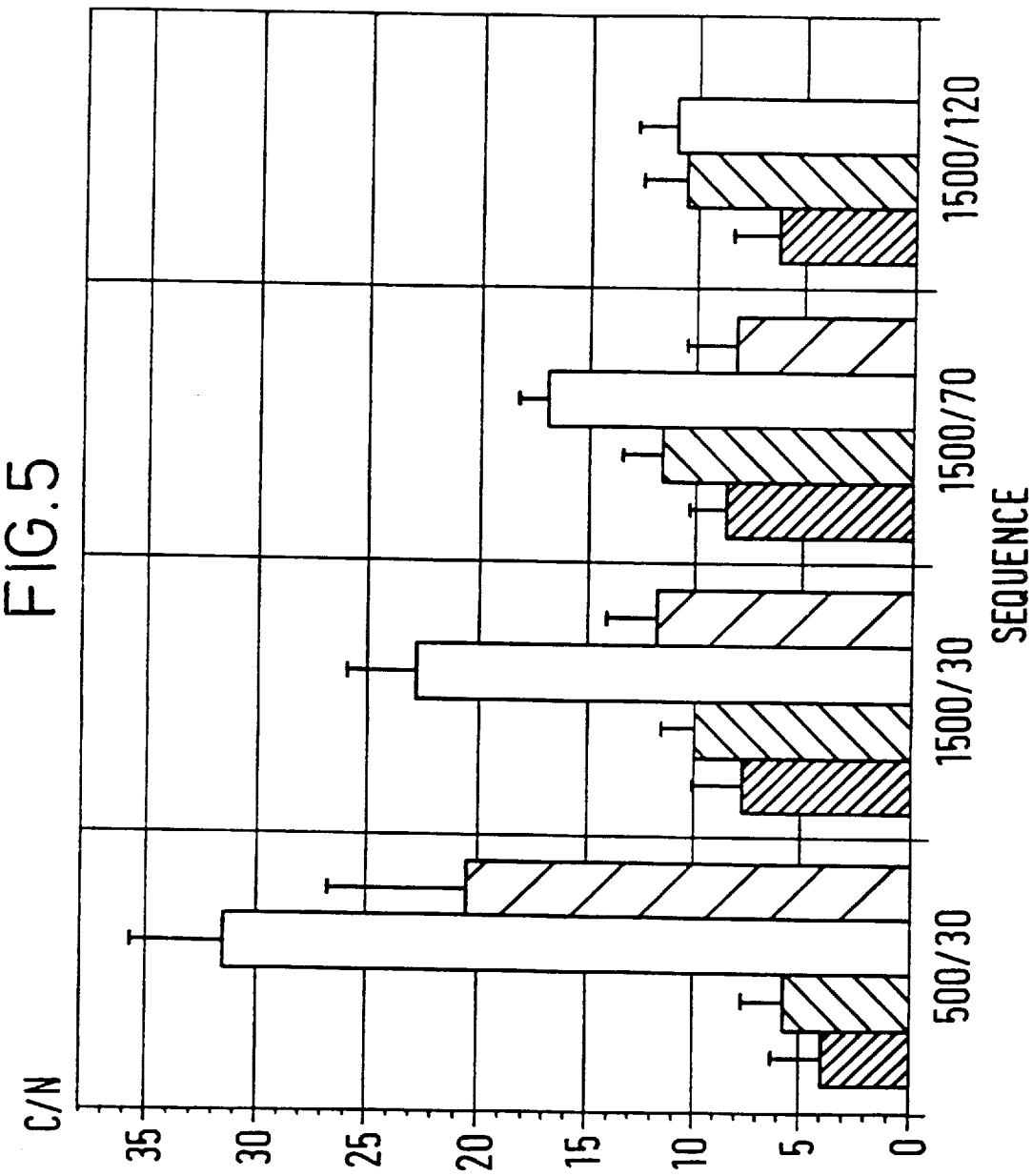

The results obtained are set forth graphically in FIGS. 4 and 5 of the accompanying drawings which display the contrast and C/N values determined as above for the four study groups at the different TR/TE sequences running from $T_1$-weighted at 500/30 to $T_2$-weighted at 1500/120. The four study groups were as follows:

Solid bar control (no contrast agent administered)

Chequered bar

Dy DTPA-BMA (1.0 mmol/kg)

Hollow bar

Double contrast Dy DTPA-BMA (1.0 mmol/kg) plus Gd DTPA-BMA (0.3 mmol/kg)

Shaded bar

Gd DTPA (0.4 mmol/kg)

It should be noted that the final group received a higher dose of the positive ECF agent than did the double contrast group. The results from this final group derive from an earlier study and are included for comparative purposes only.

The results in FIGS. 4 and 5 clearly demonstrate:

1. The negative agent does not cancel the $T_1$ enhancing effect of the positive agent in the infarcted area even though in normal tissue the negative agent would dominate.

2. Comparing the double contrast group with the group receiving the positive agent alone, even considering the higher dosage given to the latter group, the contrast and C/N between infarcted and normal myocardium is enhanced in $T_1$-weighted sequences with the double contrast approach.

3. In $T_2$-weighted sequences the double contrast position is comparable or improved relative to that with single contrast.

The concentration of metals measured in the tissues (ICP-AES) in the double contrast study were:

Gd:

Normal tissue: 0.24 μmol/g dry wt.

Infarcted area: 0.90 μmol/g dry wt.

Dy:

Normal tissue: 0.80 μmol/g dry wt.

Infarcted area: 2.87 μmol/g dry wt.

Considering the doses given (Dy: 1.0 mmol/kg and Gd: 0.3 mmol/kg) this clearly demonstrates the substantially identical pharmacokinetic distribution properties of the positive and negative agents used.

EXAMPLE 5

An analogous experiment to that described in Example 4 was performed.

Myocardial infarction was induced in 5 anaesthetized pigs of either sex (weight 25–30 kg) by ligating a diagonal branch of the left anterior descending artery (LAD), at thoracotomy. Microdialysate probes were inserted in ischemic and nonischemic myocardium. The pigs were sacrificed 2 hours after administration of contrast media. 4 hour post occlusion Gd-DTPA-BMA (0.3 mmol/kg) and Dy-DTPA-BMA (1.0 mmol/kg) were simultaneously administered in vivo with an injection time of one minute. The total occlusion time was thus 6 hours.

The microdialysate was collected every 10 minutes and measured for gadolinium and dysprosium using inductively coupled plasma atomic emission spectrometry (ICP-AES). The microdialysis equipment consisted of a CMA®/20 microdialysis probe with a 10 mm flexible membrane and a diameter of 0.5 mm (CMA AB, Stockholm, Sweden). The membrane had a 20 kD cut off. The probe was perfused with a Krebs-Ringer phosphate buffer (pH 7.4) at a speed of 2 $\mu$l/min and a dead space, in the system, of 10 $\mu$l. Sampling intervals were 10 minutes over a total time of 120 minutes yielding a sampling volume of 20 $\mu$l. One probe was inserted into the central part of the ischemic area and another probe was placed in non-ischemic myocardium in the lateral wall using the Seldinger technique to minimize mechanical injury to myocardium and probe membrane. A CMA® microdialysis pump (CMA 100) was used with two syringes to perfuse the probes.

Following sacrifice, the hearts were extirpated and rinsed in isotonic saline to remove remaining blood. The hearts were examined ex vivo at ambient temperature in the MR equipment and then cut into approximately 8 mm thick transverse slices and soaked for 10–20 minutes in a 1% aqueous solution of triphenyltetrazolium chloride (TTC) at 37° C. TTC stains non-ischemic myocardium brick red. The slices were inspected visually for unstained areas of infarction.

MR images were obtained in an identical manner to that described in Example 4.

In the transverse images, three ROI's were placed in infarcted myocardium. Four ROI's were placed in non-ischemic myocardium, two in the anterior wall and two in the posterior wall of the left ventricle. The mean signal intensity (S) was measured in each ROI. One ROI was placed anterior to the heart in an area free from visible artefacts, in order to measure the standard deviation (SD) of the background signal. These measurements were used to calculate the contrast (C) and contrast-to-noise (C/N) ratios between infarcted (inf) and non-ischemic (nonisch) myocardium using the formulae defined in Example 4.

In each heart, non-ischemic myocardium and infarction were represented by a mean value from measurements in two slices.

The longitudinal relaxation times (T1) in blood at 37° C. were measured, using a 0.47 Tesla Brucker Minispec NMR analyzer, before and after administration of the contrast agent in order to verify injection.

The total amount of gadolinium and dysprosium in samples of infarcted and non-ischemic myocardium was quantified by ICP-AES.

In addition, gadolinium and dysprosium were determined in dialysates from five pigs by ICP-AES. Twenty $\mu$l portions were sampled in plastic tubes and kept frozen until analysis. The samples were diluted to 5.02 ml with ultra-pure water. To enhance the sensitivity of measurements, an ultrasonic nebulizer was used instead of the pneumatic one. The limit of detection for the method is about 2 $\mu$g/l for both gadolinium and dysprosium in the measuring solution. This means that about 3 $\mu$mol/l can be detected in the dialysates. The emission from sodium was also measured, as this signal reveals variations in the delivery of dialysate to the sample tubes. Because of such variations, all data from the one pig had to be excluded. In addition, the gadolinium and dysprosium data from another pig, at 30 and 100 min, were excluded due to a technical failure. The contrast substances, Gd-DTPA-BMA and Dy-DTPA-BMA, both 0.5 mmol/ml, were serially diluted to achieve different concentrations and analysed and the theoretical concentrations agreed well with those observed.

Paired t-tests (two-tailed) were used to compare the gadolinium and dysprosium content, respectively, in infarcted and non-ischemic myocardium within the group. ANOVA repeated measurement analysis with Scheffe's test was used to compare the four sequences for contrast and C/N ratios in the group. One-factor ANOVA with Sheffe's test was used for comparisons of contrast ratio between the actual group and two groups (Dy-DTPA-BMA and control group) from a previous study. In addition, the extracellular concentrations of gadolinium and dysprosium were further compared with the content of gadolinium and dysprosium in tissue samples.

MR imaging. All five hearts had a well demarcated area with increased signal intensity in all sequences, corresponding to the infarcted area defined by TTC staining. In three of the pigs, the infarctions displayed an inhomogeneous signal intensity in all sequences. In these infarctions, the ROI's were placed in the regions with high signal intensity.

Figure 6:
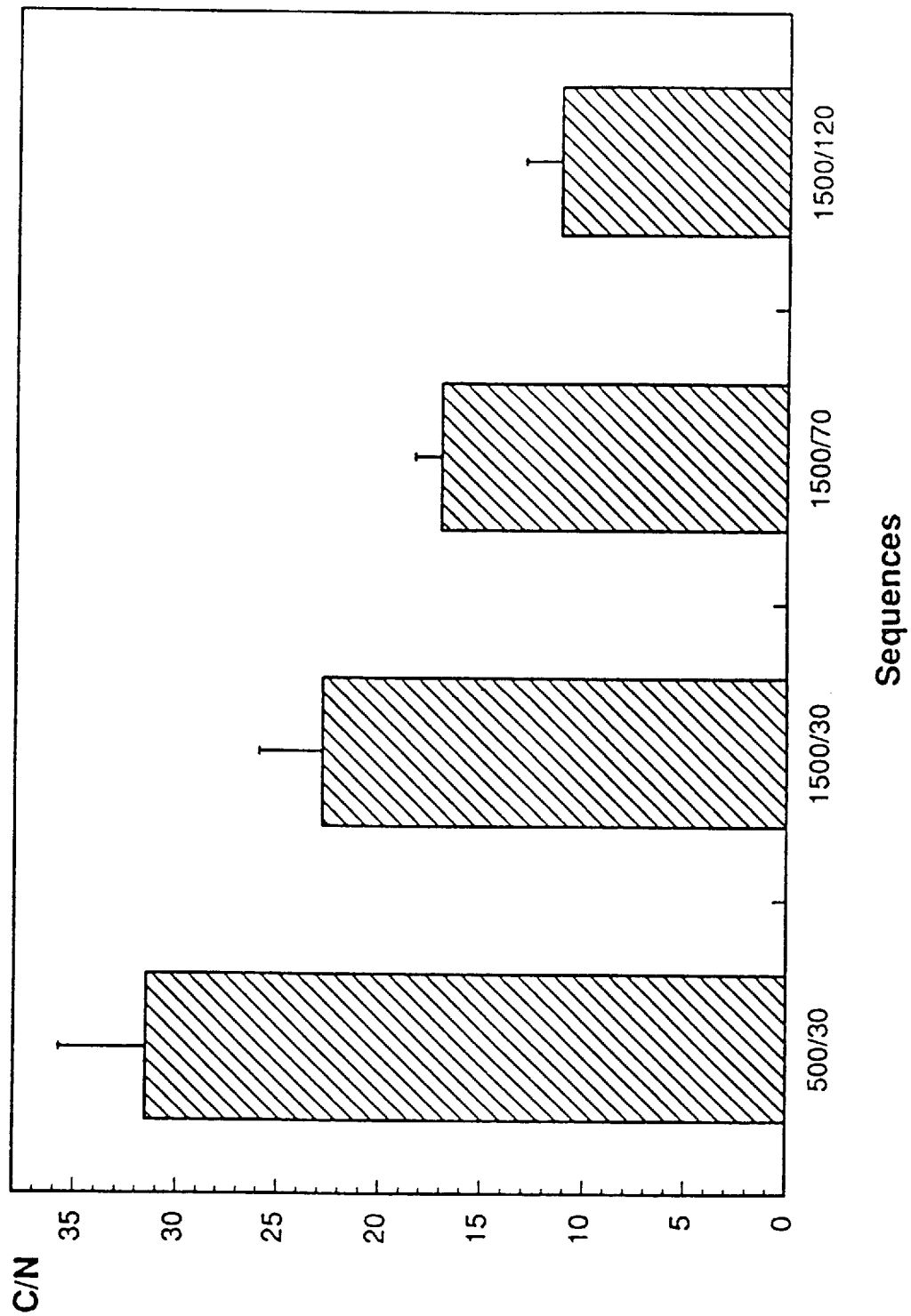
FIG. 6 shows the C/N ratios between infarcted and non-ischemic myocardium in excised hearts. The sequences TR/TE 500/30, 1500/30, 1500/70 and 1500/120 are compared in the double-contrast group (n=5, hatched bars). Each bar represents a mean value, with error bars=1 SD.

The contrast:noise (C/N) and contrast ratios determined are presented in FIGS. 6 and 7 of the accompanying drawings.

FIG. 6 shows the C/N ratios between infarcted and non-ischemic myocardium in excised hearts. The sequences TR/TE 500/30, 1500/30, 1500/70 and 1500/120 are compared in the double-contrast group (n=5, hatched bars). Each bar represents a mean value, with error bars=1 SD.

FIG. 7 shows the contrast ratios between infarcted and non-ischemic myocardium in excised hearts. The sequences TR/TE 500/30, 1500/30, 1500/70 and 1500/120 are compared in the control (n=6, white bars), Dy-DTPA-BMA (2 hour post-injection 1 mmol/kg b.w., n=6, black bars) and double-contrast groups (n=5, hatched bars). Each bar represents a mean value, with error bars=1 SD.

The measured distribution of gadolinium and dysprosium in infarcted and non-infarcted myocardium is shown in FIG. 8 of the accompanying drawings. It can be seen that there was a more than threefold higher concentration of dysprosium and of gadolinium in infarcted myocardium than in non-ischemic myocardium.

The kinetics of gadolinium and dysprosium distribution within the extracellular space (in terms of the concentrations of gadolinium and dysprosium in microdialysate from infarcted (IC) and non-ischemic myocardium (N) monitored in vivo are shown in FIGS. 9 and 10 of the accompanying drawings. After an early peak, within the first 10 minutes the concentration of gadolinium and dysprosium in the dialysate from non-ischemic myocardium diminished with time. In the dialysate from infarcted myocardium, the concentration of both contrast agents increased gradually, reaching a plateau within 20–30 minutes which was maintained for 60 minutes.

These results clearly demonstrate:

1. The accumulation of Gd-DTPA-BMA induced an enhanced infarction signal in the T1- and proton density-weighted sequences, resulting in improved infarction visualization over the situation where either no contrast agent or only Dy-DTPA-BMA was administered.

2. The signal intensity enhancement induced by Gd-DTPA-BMA was not significantly counteracted by Dy-DTPA-BMA in any of the investigated sequences, despite the fact that the Dy concentration was more than three times greater in infarcted myocardium than in non-ischemic myocardium and that in the infarctions was more than three times greater than that of gadolinium.

3. There is a lack of detectable susceptibility induced (i.e. Dy induced) signal intensity reduction effects in the infarctions.

4. Dy-DTPA-BMA did not counteract the Gd-DTPA-BMA induced enhancement of the infarcted tissue despite having a concentration which was three-times higher. (The study of Example 5 was performed by S. Nilsson, G. Wikström, A. Ericsson, M. Wikstroam, A Øksendal, A. Waldenstrøm and A. Hemmingsson of the University of Uppsala and of Nycomed Imaging AS).

EXAMPLE 6

Thirty seven Sprague Dawley rats (200–400 gm) were anaesthetized by an intraperitoneal injection of sodium pentobarbital (50 mg/kg body weight). After tracheostomy, animals were ventilated using a small animal respirator. The heart was exposed following a left thoracotomy through the 4th intercostal space and a surgical suture was used to ligate the anterior branch of the left coronary artery near its origin beneath the left atrial appendage using a snare ligature. The presence of occlusion was visually confirmed by noting the development of myocardial cyanosis. After 1 hour occlusion, reperfusion was initiated by loosening the snare ligature. A catheter was placed into a femoral vein to inject contrast media. All animals which received contrast agent were administered doses at 45 minutes of reflow. After 1 hour reperfusion, each heart was excised and rinsed in 0.9% saline, patted dry with gauze, and a cotton swab was inserted into the left ventricular cavity to expand the chamber. Each heart was wrapped in clear plastic wrap to minimise dehydration during imaging.

Images were acquired at room temprature using a GE CSI 2.0 T system. Each heart was positioned with its long axis parallel to the main magnetic field such that axial images would present short axis views of the heart. All images were obtained using a slice thickness of 2 mm, FOV of 30 mm, and a raw data matrix of 128×256 interpolated to 256×256 during reconstruction. TR/TE settings used for spin echo images are indicated below. Gradient echo images were obtained using a TR of 600 ms, with the radio frequency pulse power set very low such that no signal saturation was evident following multiple pulses and images would contain no T1 weighting.

TABLE I

MR contrast agents and imaging techniques used for each group of rats.

| | Contrast Agents | MR Imaging |
|---|---|---|
| Experimental Protocol #1 | | |
| Group 1 (n = 9) | GD + Dy | SE T1- and T2-weighted images |
| Group 2 (n = 7) | None | SE T1- and T2-weighted images |

TABLE I-continued

MR contrast agents and imaging techniques used for each group of rats.

| | Contrast Agents | MR Imaging |
|---|---|---|
| Experimental protocol #2 | | |
| Group 3 (n = 11) | Dy alone | SE T1- and T2-weighted, four-echo T2-weighted, and GRE images |
| Group 4 (n = 7) | Gd alone | SE T1- and T2-weighted, four-echo T2-weighted, and GRE images |
| Group 5 (n = 7) | None | SE T1- and T2-weighted, four-echo T2-weighted, and GRE images | n = number of animals studied within each group;
SE = spin echo;
GRE = gradient recalled echo.

To group 1 rats (n=9) were administered 0.2 mmol/kg of GdDTPA-BMA immediately followed by 1.0 mmol/kg of DyDTPA-BMA. Group 2 (n=7) received no contrast agents. Two spin-echo images were obtained from the midventricle of each heart, a T1-weighted image with TR/TE=300/20 and NEX=4, and T2-weighted image with TR/TE=3000/60 and NEX=2. After imaging, each heart was sliced at the mid-ventricular level and soaked in a 2% solution of TTC at 37° C. for 15 minutes to define myocardial infarction.

Samples of normal and infarcted myocardium were retained for analysis of Gd and Dy content by means of ICP-MS.

Group 3 (n=11) received 1.0 mmol/kg DyDTPA-BMA, group 4 (n=7) received 0.2 mmol/kg of GdDTPA-BMA and group 5 (n=7) received no contrast agents. The imaging protocol for each heart consisted of spin echo T1-weighted (TR/TE=300/20 ms, NEX=4) and T2-weighted (TR/TE=4000/80 ms; NEX=2), a set of four-echo T2-weighted images (TR=4000 ms, TE=20, 40, 60 and 80 ms, NEX=2) for estimation of regional T2 values, and a set of gradient-recalled images (TE=10, 15, 20 and 30 ms, NEX=4) for estimation of region T2* values. TTC staining of the heart was performed to verify the presence of infarction.

Signal intensities were measured from ROIs selected over infarcted and uninfarcted myocardium. The same ROIs were applied to all images obained from each heart.

Table II below summarizes the averaged signal intensities of normal and reperfused infarcted myocardium obtained from these groups.

TABLE II

Signal intensities measured on MR images and regional myocardial tissue concentration

| | Normal | Infarct |
|---|---|---|
| No contrast | | |
| (SI, arbitrary units) | (n = 7) | (n = 7) |
| T1-weighted | 83.4 ± 3.4 | 83.2 ± 4.1 |
| T2-weighted | 76.4 ± 5.0 | 90.5 ± 5.6* |

TABLE II-continued

Signal intensities measured on MR images and regional myocardial tissue concentration

|  | Normal | Infarct |
|---|---|---|
| Group I | | |
| (SI, arbitrary units) | (n = 9) | (n = 9) |
| T1-weighted | 92.8 ± 3.8 | 302.3 ± 12.6*† |
| T2-weighted | 19.6 ± 2.4† | 43.7 ± 2.9*† |
| gadolinium content | (n = 3) | (n = 3) |
| ($\mu$mol/g wet wt) | 0.13 ± 0.04 | 0.32 ± 0.06 |
| dysprosium | (n = 3) | (n = 3) |
| ($\mu$mol/g wet wt) | 0.59 ± 0.15 | 1.48 ± 0.18 |

SI = signal intensity;
*$p < 0.05$ in comparison between value in normal and infarcted myocardium;
†$p < 0.05$ in comparison with respective value of no contrast group.

Also shown in Table II are tissue content of gadolinium and dysprosium measured in the myocardial regions of group 1. In group 2 there was no difference in signal intensity between normal and infarcted myocardium on T1-weighted images, while on T2-weighted images the signal of the infarcted region was slightly higher than normal myocardium (Table II). In comparison, in group 1 the hyperintense region noted on T1- and T2-weighted images were identical and corresponded in location and extent to the infarcted region defined on histochemical stain. (See Table II and FIG. 11 of the accompanying drawings.)

Figure 11:
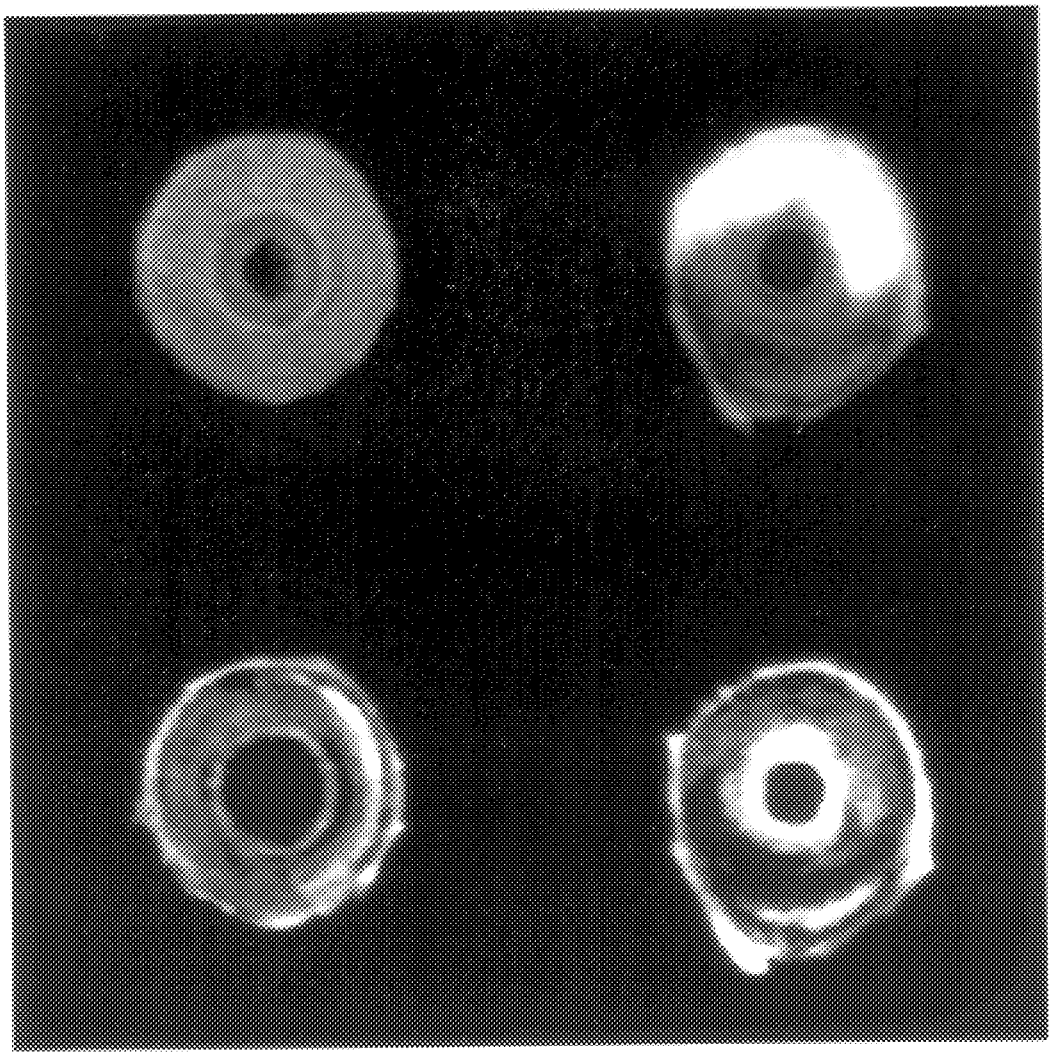
FIG. 11 is a photograph which shows unenhanced short axis T1-(upper left) and T2-weighted (lower left) images, and enhanced T1-(upper right) and T2-weighted (lower right) spin echo images with both GdDTPA-BMA and DyDTPA-BMA.

FIG. 11 shows unenhanced short axis T1- (upper left) and T2-weighted (lower left) images, and enhanced T1- (upper right) and T2-weighted (lower right) spin echo images with both GdDTPA-BMA and DyDTPA-BMA. These images were obtained from 2 different hearts (group 1) subjected to 1 hour coronary occlusion followed by 1 hour reperfusion.

Figure 12:
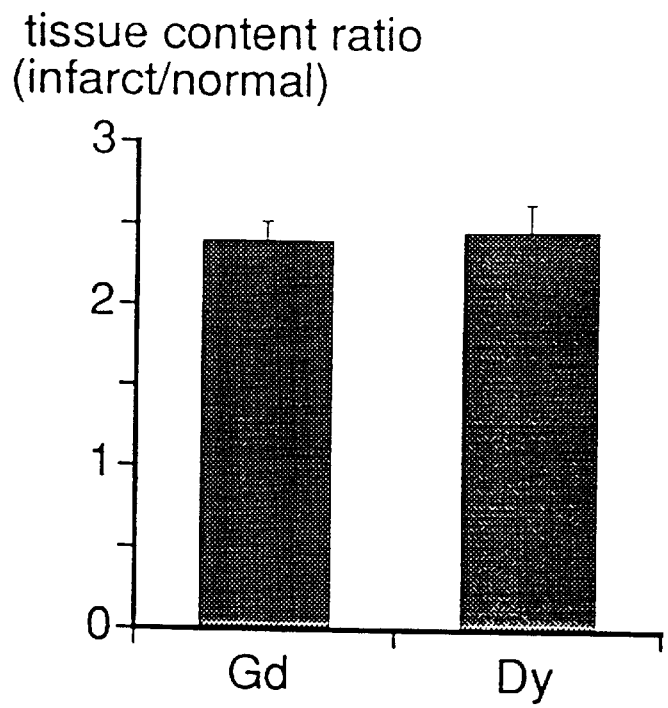
FIG. 12 is a bar graph which shows the tissue concentration ratios of both Gd and Dy for infarcted to normal myocardium.
Figure 13:
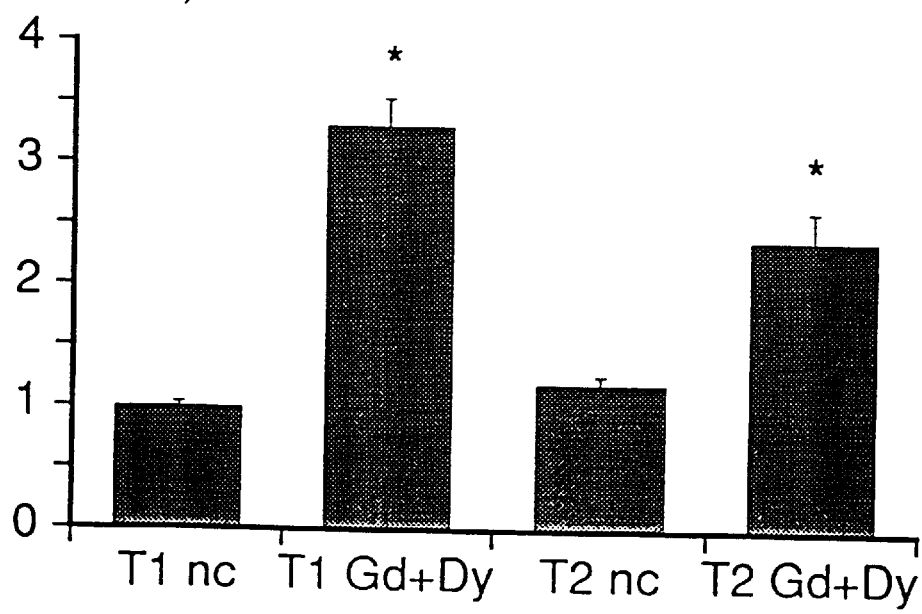
FIG. 13 is a bar graph which shows the observed myocardium contrast (signal intensity of injured myocardium/signal intensity of non-ischemic myocardium) on unenhanced and enhanced T1- and T2-weighted spin echo images with both GdDTPA-BMA and DyDTPA-MBA.

The substantial enhancement of the reperfused infarction on T1-weighted images was associated with commensurably greater content of gadolinium in that region than in normal myocardium. On the other hand, the same region exhibited a smaller signal loss than in normal myocardium on T2-weighted images despite a greater amount of dysprosium in the infarcted zone (Table II). FIG. 12 shows the tissue concentration ratios of both Gd and Dy for infarcted to normal myocardium. FIG. 13 shows the observed myocardial contrast (signal intensity of injured myocardium/signal intensity of non-isochemic myocardium) on unenhanced and enhanced T1- and T2-weighted spin echo images with both GdDTPA-BMA and DyDTPA-BMA.

A series of gradient recalled and spin echo MR images were obtained to resolve the effects of GdDTPA-BMA on T2-weighted images and DyDTPA-BMA on T1-weighted images and also to more thoroughly characterize the differences in contrast media-induced T2 and T2* enhancement between infarcted and normal myocardium. Table III summarises the observed alterations in regional signal intensity and relaxation rates following administration of either GdDTPA-BMA or DyDTPA-BMA.

TABLE III

Signal intensities and relaxation rate values measured on MR images

|  | GRE | SE T1 | SE T2 | T2 (msec) | T2* (msec) |
|---|---|---|---|---|---|
| No contrast (n = 7) | | | | | |
| normal | 141 ± 22 | 88 ± 4 | 49 ± 5 | 36.6 ± 0.6 | 19.1 ± 2.3 |
| infarct | 177 ± 37 | 92 ± 5 | 59 ± 7 | 41.7 ± 1.5 | 27.6 ± 1.9* |
| DyDTPA-BMA (n = 11) | | | | | |
| normal | 105 ± 18 | 88 ± 7 | 12 ± 1† | 25.9 ± 0.6 | 9.4 ± 0.5† |
| infarct | 191 ± 34* | 141 ± 14*† | 42 ± 4*† | 35.8 ± 1.0*† | 17.7 ± 1.2*† |
| GdDTPA-BMA (n = 7) | | | | | |
| normal | 200 ± 40 | 184 ± 21† | 42 ± 4 | 34.7 ± 0.7† | 17.1 ± 2.2 |
| infarct | 185 ± 49 | 350 ± 34*† | 35 ± 7† | 31.1 ± 1.2*† | 13.2 ± 1.5*† |

GRE = gradient recalled echo images;
SE T1 = spin echo T1-weighted images;
SE T2 = spin echo T2-weighted images;
*$p < 0.05$ in comparing value for reperfused infarction versus normal myocardium;
†$p < 0.05$ in comparing value with respective value for no contrast group.

Figure 14:
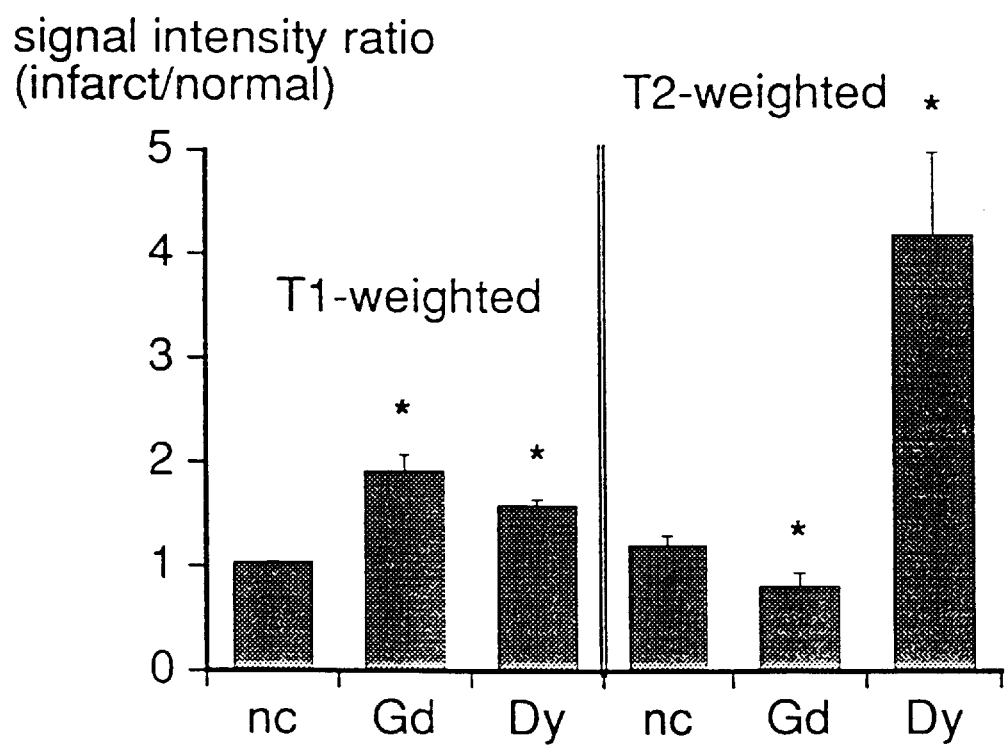
FIG. 14 is a bar graph which shows the ratios of signal intensity of reperfusad infarction to that of normal myocardium for Gd and Dy alone and in the presence of administered contrast agent (NC).

FIG. 14 of the accompanying drawings shows the ratios of signal intensity of reperfused infarction to that of normal myocardium for Gd and Dy alone and in the absence of administered contrast agent (NC). It was found that on T1-weighted images, both GdDTPA-BMA and DyDTPA-BMA caused significant differential enhancement such that the reperfused infarction was delineated as a hyperintense region. Enhancement of the infarcted region caused by GdDTPA-BMA was significantly less than that noted when both agents were present (compare FIGS. 13 and 14). On T2-weighted images, the infarcted region was also delineated by both agents. In hearts treated with GdDTPA-BMA, signal intensity of the infarcted region was significantly reduced compared to hearts with no contrast while signal in the normal region was not different from that of hearts with no contrast (see Table III, and FIG. 14). DyDTPA-BMA caused great suppression of normal myocardium signal and much less reduction in signal of the infarcted region (Table II), producing greater contrast between the two regions than was noted when both agents were administered (compare FIGS. 13 and 14).

These results clearly demonstrate:

1. When both contrast agents were administered, signal intensity of reperfused infarction on T1-weighted images was homogeneously enhanced relative to normal myocardium, indicating delivery of the T1 agent to the reperfused infarction.

2. Signal loss on T2-weighted images was significantly greater in non-ischemic myocardium than in reperfused infarcted myocardium, delineating the injured region as a relatively bright zone.

3. Concentrations of both Gd and Dy were approximately 2.5 fold greater in reperfused infarcted myocardium than in normal myocardium, consistent with a larger contrast agent distribution volume in reperfused infarction.

4. The combination of signal augmentation of the infarcted region provided by the T1 agent and signal reduction of normal myocardium provided by the T2 agent provided greatly enhanced contrast enabling clear delineation of the infarcted region.

(The study of Example 6 was performed by J. F. H. Geschwind, M. F. Wendland, M. Saeed, K. Lauerma, N. Derugin and C. B. Higgins of UCSF.)

We claim:

1. An image contrast enhancing parenterally administrable composition for magnetic resonance imaging comprising a physiologically tolerable, extracellularly distributing, paramagnetic positive contrast agent and a physiologically tolerable, extracellularly distributing, paramagnetic negative contrast agent which in use distribute into the vascular bed and interstitium.

2. An image contrast enhancing composition as claimed in claim 1 wherein said positive and negative contrast agents are present in a mole ratio of from 1:1 to 1:10.

3. An image contrast enhancing composition as claimed in claim 1 wherein said positive and negative contrast agents are present in a mole ratio of from 1:2 to 1:6.

4. An image contrast enhancing composition as claimed in claim 1 wherein said positive and negative contrast agents are present in a mole ratio of from 1:3 to 1:4.

5. A composition as claimed in claim 1 wherein said positive agent is a complex of a metal selected from the group consisting of Gd, Fe, Ho, Mn, Cr and Er, and wherein said negative agent is a complex of a metal selected from the group consisting of Tb, Sm or Dy.

6. A composition as claimed in claim 1 wherein said positive agent is a complex of a metal ion selected from the group consisting of $Gd^{3+}$, $Cr^{3+}$, $FE^{3+}$ and $Mn^{2+}$, and wherein said negative agent is a complex of $Dy^{3+}$.

7. A method of generating a contrast enhanced image of a human or non-human animal body which comprises parenterally administering to said body a first and a second paramagnetic contrast agent having substantially the same biodistribution and being physiologically tolerable extracellular fluid (ECF) agents which distribute into the vascular bed and interstitium and generating a magnetic resonance image of a part of said body into which said agents have distributed with a substantially uniform concentration ratio therebetween, one of said agents being a positive contrast agent and the other being a negative contrast agent, whereby enhanced contrast between normal tissue and tissue in which cell membrane integrity has been reduced or destroyed is obtained.

8. A method as claimed in claim 7 wherein said positive agent is a complex of a metal selected from the group consisting of Gd, Fe, Ho, Mn, Cr and Er.

9. A method as claimed in claim 7 wherein said positive agent is a complex of a metal ion selected from the group consisting of $Gd^{3+}$, $Cr^{3+}$, $Fe^{3+}$ and $Mn^{2+}$.

10. A method as claimed in claim 7 wherein said negative agent is a complex of a metal selected from the group consisting of Tb, Sm or Dy.

11. A method as claimed in claim 7 wherein said negative agent is a complex of $Dy^{3+}$.

12. A method as claimed in claim 7 wherein said first and second contrast agents are administered together or within 20 minutes of each other.

13. A method as claimed in claim 7 wherein said positive agent is a complex of a metal selected from the group consisting of Gd, Fe, Ho, Mn, Cr and Er, and wherein said negative agent is a complex of a metal selected from the group consisting of Tb, Sm or Dy.

14. A method as claimed in claim 7 wherein said positive agent is a complex of a metal ion selected from the group consisting of $Gd^{3+}$, $Cr^{3+}$, $FE^{3+}$ and $Mn^{2+}$, and wherein said negative agent is a complex of $Dy^{3+}$.

15. A method as claimed in claim 7 comprising administering to said body a contrast medium comprising said first and said second contrast agent whereby said first and second contrast agents are administered simultaneously.

* * * * *